(12) United States Patent
Attinger et al.

(10) Patent No.: US 8,465,706 B2
(45) Date of Patent: Jun. 18, 2013

(54) ON-DEMAND MICROFLUIDIC DROPLET OR BUBBLE GENERATION

(75) Inventors: Daniel Attinger, New York, NY (US); Jie Xu, New York, NY (US)

(73) Assignee: Trustees of Columbia University in the City of New York, New York, NY (US)

( * ) Notice: Subject to any disclaimer, the term of this patent is extended or adjusted under 35 U.S.C. 154(b) by 485 days.

(21) Appl. No.: 12/642,434

(22) Filed: Dec. 18, 2009

(65) Prior Publication Data

US 2010/0163412 A1 Jul. 1, 2010

Related U.S. Application Data

(63) Continuation-in-part of application No. PCT/US2008/007711, filed on Jun. 20, 2008.

(60) Provisional application No. 60/969,037, filed on Aug. 30, 2007, provisional application No. 61/032,401, filed on Feb. 28, 2008, provisional application No. 61/042,194, filed on Apr. 3, 2008, provisional application No. 61/047,034, filed on Apr. 22, 2008, provisional application No. 60/936,428, filed on Jun. 20, 2007.

(51) Int. Cl.
*G01N 15/06* (2006.01)
*G01N 33/00* (2006.01)
*G01N 33/48* (2006.01)

(52) U.S. Cl.
USPC .......... 422/505; 422/68.1; 422/502; 422/503; 422/504; 422/509; 436/43; 436/180

(58) Field of Classification Search
USPC ... 422/68.1, 502, 503, 504, 505, 509; 436/43, 436/180
See application file for complete search history.

(56) References Cited

U.S. PATENT DOCUMENTS

| 4,877,745 A | 10/1989 | Hayes et al. |
| 2002/0125424 A1 | 9/2002 | Ellson et al. |
| 2007/0003442 A1 | 1/2007 | Link et al. |

FOREIGN PATENT DOCUMENTS

WO WO-2008156837 A1 12/2008

OTHER PUBLICATIONS

"International Application Serial No. PCT/US2008/007711, International Search Report and Written Opinion mailed Sep. 11, 2008", p. 220.
Xu, J., et al., "Drop on Demand in a Microfluidic Chip", Journal of Micromechanics and Microengineering, 18, (Jun. 2008), 1-10.

*Primary Examiner* — Brian J Sines
(74) *Attorney, Agent, or Firm* — Schwegman Lundberg Woessner P.A.

(57) ABSTRACT

Microfluidic systems and methods can dispense single or multiple fluid particles (such as a gas or other fluid bubble) or an encapsulated particle (e.g., a bead or biological cell) into a microchannel.

14 Claims, 9 Drawing Sheets

ON-DEMAND MICROFLUIDIC DROPLET OR BUBBLE GENERATION

CLAIMS OF PRIORITY

This application is a Continuation-in-Part of International Application No. PCT/US2008/007711, filed Jun. 20, 2008 which claims the benefit of priority to U.S. Provisional Application No. 60/936,428, filed Jun. 20, 2007; U.S. Provisional Application No. 61/969,037, filed Aug. 30, 2007; U.S. Provisional Application No. 61/032,401, filed Feb. 28, 2008; U.S. Provisional Application No. 61/042,194, filed Apr. 3, 2008; and U.S. Provisional Application No. 61/047,037, filed Apr. 22, 2008, all of which are incorporated herein by reference in their entireties, and the benefit of priority of each is claimed herein.

STATEMENT REGARDING FEDERALLY SPONSORED RESEARCH OR DEVELOPMENT

This invention was made with government support under award numbers 0449269, 0622862, and 0701729 from the National Science Foundation (NSF). The government has certain rights in this invention.

TECHNICAL FIELD

This document pertains generally to microfluidics and more particularly, but not by way of limitation, to on demand-microfluidic droplet, bubble, or other particle generation.

BACKGROUND

Microfluidics deals with controlling fluids in small structures, such as a sub-millimeter scale, in certain examples.

OVERVIEW

This document discusses, among other things, microfluidic systems and methods for on-demand individually dispensing of single or multiple fluid particles (such as a liquid or other fluid drop or a gas or other fluid bubble) into one or more microchannel of a microfluidic apparatus, such as a microfluidic chip.

The present inventors have recognized, among other things, that microfluidic applications can benefit from an ability to dispense or control small fluid particles, such as drops or bubbles, in a microchannel, particularly if this can be done on-demand with high timing accuracy or volume accuracy.

Furthermore, the present inventors have recognized that microfluidic applications can benefit from an ability to encapsulate one or more small particles (e.g., beads or biological cells) in one or more small liquid drops for purposes such as manipulating or analysis. Furthermore, it would be advantageous to be able to dispense an encapsulated bead or cell in an on demand fashion.

One approach to dispensing drops can involve electrokinetic pinching, such as to inject an individual liquid plug on demand in a miscible liquid. However, this technique does not prevent diffusion of the plug content in the surrounding liquid.

Another approach to dispensing drops can use segmented flow transport, such as to transport two immiscible fluids along a microchannel in the form of a train of successive compartments of the different fluids. This segmented flow transport technique can enhance mixing within a single compartment while preventing diffusion between two adjacent compartments. However, the segmented flow transport technique can have a possible drawback in that it generates a train of particles rather than providing enough control to dispense, on-demand, one or more fluid particles. Segmented flow can be used to provide monodisperse drops that can have applications in chemistry and material processing, such as to allow the manufacture of novel materials, the manufacture of particles with precise shape control, manufacture of armored bubbles, manufacture of silica or other nanoparticles, or the handling of exothermic reactions.

The present inventors have recognized a need for an approach that can generate a single particle (such as a drop or a bubble) or a single encapsulated particle (such as a drop or bubble that includes one or more beads or biological cells), on-demand, in an immiscible fluid, or to individually generate multiple particles or encapsulated particles on-demand in the immiscible fluid.

Accordingly, the present inventors have developed, among other things, apparatuses and methods that can dispense and transport individual drops or bubbles in a microfluidic apparatus, such as a microfluidic chip, on-demand, which can provide precise timing and reproducible control of the volume, such as over almost three orders of magnitude (e.g., from about 25 pL to about 4.5 nL).

Unlike the segmented flow approach of monodisperse droplet generation, the present microfluidic, in-chip, drop-on-demand approach can avoid any need to sort or recycle unwanted droplets and can provide electronic (e.g., nanosecond accuracy) control of the timing of the actuation control signal for actuating droplet generation, which allows coordination with other events occurring in the microfluidic chip, such as heat and mass transport, or the transit of one or more particles (e.g., biologic cells, solid particles, etc.). The present microfluidic, in-chip, drop-on-demand approach can also provide analog control of the droplet size and velocity, such as by varying the time or shape of the actuation pulse. The present microfluidic, in-chip, drop-on-demand approach can also provide digital control of the droplet size, such as by merging several droplets (e.g., of equal size).

The present inventors have also recognized that the drop-on-demand techniques can also be used to encapsulate one or more small particles, so the present approach can also include apparatuses and methods that can dispense and transport individual drops or bubbles that encapsulate one or more small particles (e.g., beads or biological cells) in a microfluidic apparatus on demand. One advantage of this encapsulating technique is that it can permit a protein secreted by a cell to stay in a relatively close vicinity to the cell (e.g., within the aqueous drop), which can be useful for single-cell analysis. The ability to encapsulate on demand a single cell into a picoliter sized volume, without the need to generate a long train of single cells in a train of respective drops, is particularly useful for single-cell analysis.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, dispensing of individual drops, particles, or bubbles, such as on-demand inside one or more channels of a microfluidic apparatus such as a microfluidic chip.

The present inventors have recognized, among other things, that microfluidic applications can benefit from an ability to dispense or control small fluid particles, such as drops or bubbles, in a microchannel, particularly if this can be done with high timing accuracy or volume accuracy.

One approach can involve electrokinetic pinching, such as to inject an individual liquid plug on demand in a miscible liquid. However, this technique does not prevent diffusion of the plug content in the surrounding liquid.

Another approach can use segmented flow transport, such as to transport two immiscible fluids along a microchannel in the form of a train of successive compartments. This segmented flow transport technique can enhance mixing within a single compartment while preventing diffusion between two adjacent compartments. However, the segmented flow transport technique can have a possible drawback in that it generates a train of particles rather than a single fluid particle.

The present inventors have recognized a need for an approach that can generate a single particle (such as a drop or a bubble), on demand, in a fluid that is immiscible with the particle on a time scale of interest (e.g., the time it takes for the particle to travel a desired distance or the time it takes for the particle to travel through an application or system).

Accordingly, the present inventors have developed, among other things, apparatuses and methods that can dispense and transport individual drops or bubbles in a microfluidic apparatus, such as a microfluidic chip, on-demand, which can provide precise timing and reproducible control of the volume, such as over almost three orders of magnitude (e.g., from about 25 pL to about 4.5 nL).

Figure 1A:
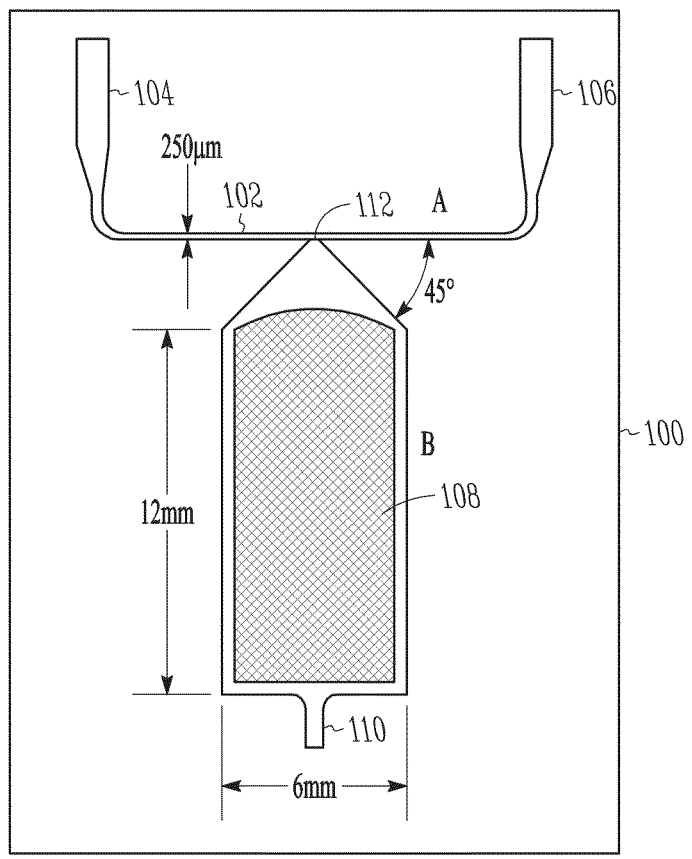
FIG. 1A shows a top view of an example of portions of a microfluidic apparatus.

FIG. 1A shows a top view of an example of portions of a microfluidic apparatus. In this example, the microfluidic apparatus can include a microfluidic chip 100. The microfluidic chip 100 can include a channel 102 including an inlet 104 and an outlet 106. One or more reagent chambers 108 can include an inlet 110 and a microfluidic nozzle outlet 112. The nozzle outlet 112 can be in fluid communication with the channel 102, such as at a location between the inlet 104 and the outlet 106 of the channel 102. The illustrative example of FIG. 1A shows a 6 millimeter wide by 12 millimeter long reagent chamber 108, which can taper down (such as at the 45 degree angle shown) to the microfluidic nozzle outlet 112, which can be about 50 μm across in the illustrative example of FIG. 1A.

In certain examples, the volume of the one or several reagent chambers 108 can be on the order of a microliter, and the microfluidic nozzle outlet 112 can vary in size, such as from about 25 μm across to about 100 μm across. In certain examples, multiple reagent chambers 108 can include respective microfluidic nozzle outlets 112 to the channel 102 at different locations along the length of a portion of the channel 102, or at the same location along the length of a portion of the channel 102, such as for a case in which two different reagent chambers 108 are located across the channel 102 from each other (see, e.g., image sequence (c) in FIG. 7), providing opposing nozzle outlets 112 to the channel 102 on opposite sides of the channel 102 at the same location along the length of a portion of the channel 102.

Syringes or other fluid introduction devices can be respectively coupled to the inlet 104 of the channel 102, or to the inlet 110 of the reagent chamber 108. For example, a first syringe 114 can be used to introduce a fluid (e.g., hexadecane) into the channel 102. A second syringe 116 can be used to introduce an aqueous reagent into the inlet 110 of the reagent chamber 108. The fluid introduced into the channel 102 and the aqueous reagent introduced into the reagent chamber 108 can be selected to be immiscible, such that they tend not to mix with each other. Therefore, a stable meniscus can form at the interface therebetween, such as at the opening of the nozzle outlet 112 to the channel 102. In some examples, reagent chamber 108 can contain particles (e.g., beads or biological cells) in a solution (e.g., an aqueous solution). In some examples, the fluid introduced into the channel 102 can be one that will not have a deleterious effect (e.g., harming a biological cell and/or denaturing proteins of interest) on particles of interest that may be encased in the bubbles formed from the solution in chamber 108.

Figure 1B:
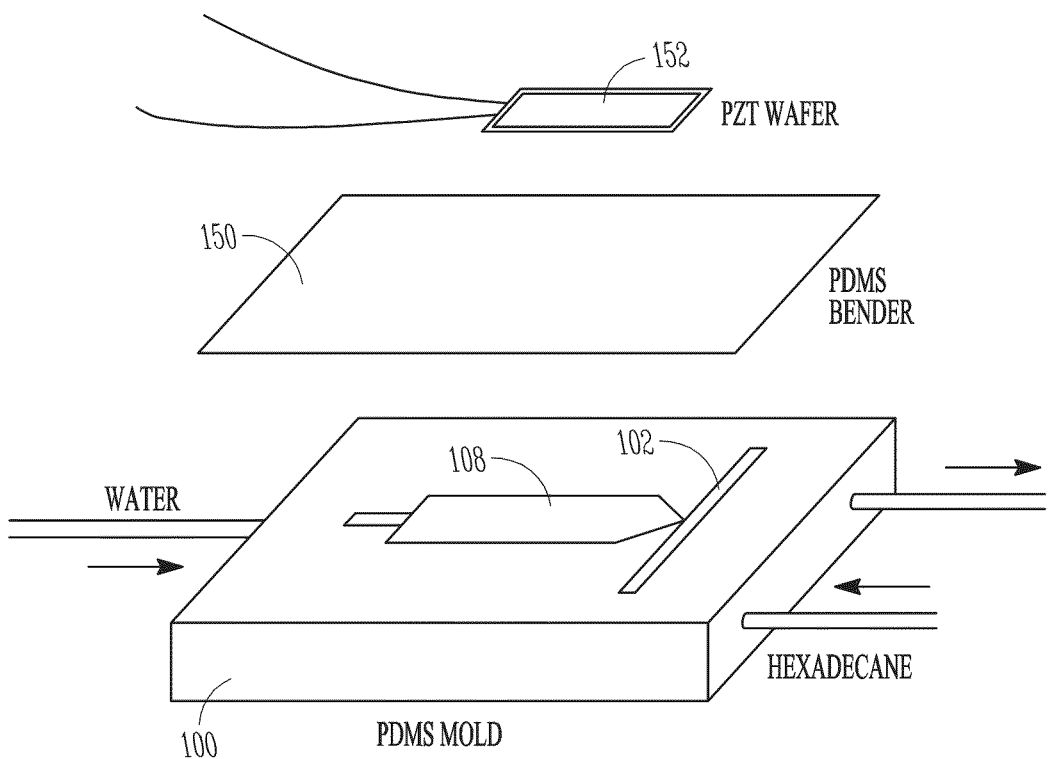
FIG. 1B shows an exploded view of a schematic example of portions of the microfluidic apparatus of FIG. 1A.

FIG. 1B shows an exploded view of a schematic example of portions of the microfluidic apparatus of FIG. 1A. In the example of FIG. 1B, the microfluidic chip 100 includes the channel 102 and at least partially compliant reagent chamber 108. An overlying sealing compliant PDMS bender membrane 150 can be affixed to the top surface of the microfluidic chip 100. In the example of FIG. 1B, the reagent chamber 108 includes compliant PDMS walls. However, hard plastic walls can also be used for the reagent chamber 108, such as together with the compliant membrane 150. A PZT or other piezoelectric or other actuator 152 can be affixed upon the compliant membrane 150, such as above reagent chamber 108 to induce volumetric changes thereto.

In certain examples, the height of the channel 102 or that of the nozzle outlet 112 can be in the 50-100 μm range. The microfluidic chip 100 can be sealed on the top with a thin membrane 150, in certain examples, such as shown in FIG. 1B. An actuator 152 can be placed on top of the membrane 150, such as shown in FIG. 1B. A control signal can be provided to actuate the actuator 152 to controllably influence or modify the volume of the reagent chamber 108, and to permit on-demand release of a particle (such as a drop or bubble) of the aqueous reagent or other contents of the reagent chamber 108 into the channel 102. In certain examples, a piezoelectric bimorph or other piezoelectric actuator 152 can be used to modify the volume of the reagent chamber 108. However, one or more other actuators 152 (e.g., bubble-jet or other thermal, optoacoustic, etc.) can also be used, if desired, to modify the volume of the reagent chamber 108.

In an illustrative experimental example, microfluidic chips 100 were fabricated in the clean room of Columbia University using soft lithography. First, a 10 μm thin base layer of SU-8 resin (MicroChem) was spun and cured on a substrate, such as a silicon wafer. However, a different thickness, material, application technique, or substrate can be used, if desired. On top of that base layer, a 50-100 μm overlayer of SU-8 2050 was cured with patterns transferred from a mask (CAD/Art Services Inc.) to form a "master". However, a different overlayer thickness, material, application technique, or patterning technique can be used, if desired. Without being bound by theory, this method using the initial base layer can improve adhesion of SU-8 to the wafer or other substrate. The microfluidic chip 100 can then be manufactured from the master, such as by using a PDMS Sylgard 184 Kit (Dow Corning). The one or more channels 102 or one or more reagent chambers 108 in the resulting microfluidic chip 100 can be sealed, such as by a thin (e.g., 180 μm thick) membrane 150, such as can be made from spin-coated PDMS. Individual piezoelectric actuators 152 can be placed on top of the membrane 150 such as at corresponding locations above individually actuated reagent chambers 108. This can permit modulating the volume of the one or more reagent chambers 108. In certain examples, the one or more piezoelectric actuators 152 can include commercially available bimorph actuators, which can be made of two PZT layers bonded on a thin brass layer, which can exhibit a total thickness T of about 0.51 mm, with a length and width that is slightly smaller than the chamber dimensions as shown in FIG. 1A, if desired. In the experimental example, one actuator 152 was adhered on top of each reagent chamber 108, such as by using a 90 μm layer of double-sided tape.

Figure 2:
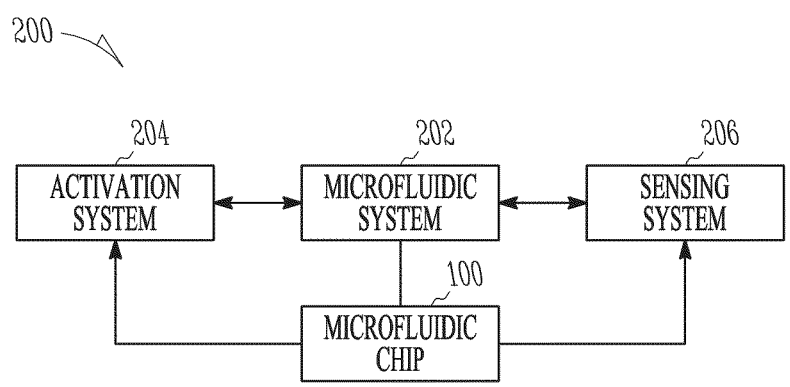
FIG. 2 shows an example of an experimental setup.

FIG. 2 shows an example of an experimental setup 200. In this example, the experimental setup can include a microfluidic system 202, an actuation system 204, and a sensing system 206. The microfluidic system 202 can include a microfluidic device, such as a microfluidic chip 100 ("a"). Syringes can be used to fill the main channel 102 with hexadecane or other desired substance or to control injection of aqueous plugs into the dispensing reagent chamber 108.

In an example, the actuation system 204 can include a 20 MHz function generator (e.g., Agilent, 33120A). This function generator ("d") can be coupled to a 1 MHz 40 W amplifier (e.g., Krohn-Hite, 7600M). An amplifier ("e") can generate high-voltage driving pulses for the piezoelectric actuators 152. The piezoelectric actuators 152 can be glued on or otherwise attached to the microfluidic chip 100, such as onto the thin membrane, respectively located over the individual reagent chambers 108.

In an example, the sensing system 206 can include a high-speed high-resolution imaging system. This can include an Olympus IX-71 microscope ("c") and a high-speed camera ("b") (e.g., Redlake MotionXtra HG-100K), such as that can provide up to 100,000 frames per second. Microfluidic devices involving electrokinetic pinching, segmented flow, or digital microfluidics can require actuation and detection devices that can be orders of magnitude larger and more expensive than the microfluidic chip itself, such as high-voltage power supplies, syringe pumps, drive electronics or microscopes. The present inventors have recognized, among other things, that it can be desirable to reduce the size or cost of microfluidic actuators or sensors, such as by using simple, portable microfluidics devices or CMOS-based sensing chips.

Figure 3:
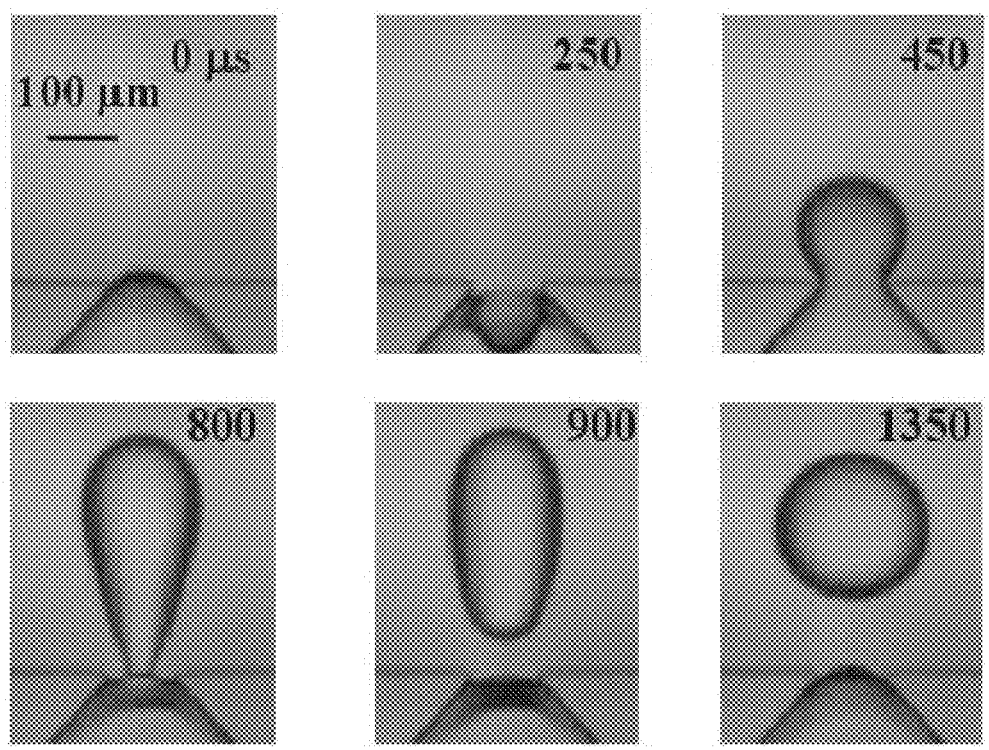
FIG. 3 shows an example of images of experimental results of using a microfluidic chip like that of FIG. 1 and the experimental setup of FIG. 2.

FIG. 3 shows an example of images of experimental results, such as of using a microfluidic chip similar to the microfluidic chip 100 of FIG. 1, and using the experimental setup 200 described in FIG. 2. FIG. 3 shows examples of stages depicting the formation of a 1 nL drop from a 50 μm across nozzle. Once the drop has been dispensed from the reagent chamber 108 into the main channel 102, the drop can be transported in the channel 102 using viscous drag of the immiscible fluid (e.g. hexadecane) in the channel 102. In certain examples, the drop can be transported in the channel 102 toward the shooting area of another nozzle 112, e.g., of a different "downstream" reagent chamber 108, where another drop of another (same or different) reagent can be dispensed and mixed with the initial drop. In this way, a determined sequence of mixings or reactions can be performed, such as by bringing the original drop in front of the nozzles 112 of several dispensing reagent chambers 108, respectively containing prescribed reagents. In certain examples, two nozzles can share the same shooting range and reagent mixing can occur without moving the drop, such as where the two nozzles face each other on opposite sides of the channel 102, such as shown in image sequence (c) of FIG. 7. Drop volumes can be as small as a few picoliters (pL). The internal flow associated with the motion of the drops in a channel 102 can enhance mixing and diffusion, such as when two different drops are combined. In certain examples, the needed reagent volume (or "dead volume") can be relatively small. For example, a chamber of 20 mm×5 mm×50 μm, which can be fed by a tube of 300 μm diameter and length L=1 cm, represents a dead volume of 8 μL, which corresponds to enough "ammunition" substance to shoot 10,000 80-pL drops.

Example of Energy Considerations

While a full study of how energy is transmitted from the moving actuator 152 to the resulting drop via the soft rubber membrane 150 and the fluid in the 3-dimensional, flexible reagent chamber 108 is out of the scope of this document, we can compare the energy needed to form a drop with the deformation energy of the actuator (without being bound by the theory presented herein). Generating a microdrop of water in oil can involve the sudden excitation of a piezoelectric actuator 152, such as to compress or expand the reagent chamber 108. This excites the water-oil interface, between the nozzle 112 and the channel 102. The water-oil interface eventually breaks up and forms a drop. The minimum energy $U_d$ needed to form such a drop can in certain examples be described as $U_d = U_s$, where $U_s$ is the surface energy of the newly created drop. The surface energy can be calculated as $U_s = \pi d^2 \gamma$, with properties such as shown by way of example, but not by way of limitation, in Table 1.

TABLE 1

Physical properties and examples of typical values

| Symbol | Physical property | Example of Typical Value |
|---|---|---|
| γ | Surface tension at the water-hexadecane interface | 52.5 mJ/m² |
| $d_{31}$ | Piezoelectric strain coefficient | $190 \times 10^{-12}$ Pa |
| Y | Piezoelectric elastic modulus | $6.2 \times 10^{10}$ Pa |
| ρ | PZT density | 7750 kg/m³ |
| E | Electric field applied across actuator | 400 kV/m |
| L, B, T | Actuator length, width, thickness | 12-20, 3-4, 0.51 mm |

The drop formation energy can be provided by the flexion work of the actuator, which can be approximated as W=0.5F·D, where the force $F=3d_{31}YBT^2E/(8L)$ and the maximum displacement $D=3d_{31}L^2E/(8T)$ are function of the properties described in Table 1. Also, in certain examples, the actuator 152 is flexing in its first mode, with one end anchored and the other immobile along the z-direction so that D, the maximum z-deflection, occurs in the middle of the length of the actuator 152. For a 5 nL drop generated from a reagent chamber 108 using a 20 mm×3.5 mm actuator 152, the efficiency $U_d/W$ can correspond to 0.9%. This efficiency is relatively low, but is a reasonable value considering the viscous energy dissipation in the connecting tape, the thin PDMS membrane 150 over the reagent chamber 108, the reagent chamber 108, and the fluid in the main channel 102.

Example Considering Motion of the Actuator

Given the compliant character of PDMS, an oscillation of relatively large amplitude can be needed to produce drops. Piezoelectric bimorph actuators 152 can provide large deformation. For example, the out-of-plane deformation (called here the z-displacement) of a piezoelectric bimorph can be on the order of tens of micrometers for an L=20 mm long piezoelectric bimorph, assuming the actuator width w<<L. A parameter in the actuation design can include the eigenfrequency of the actuator, which can limit the speed of deformation. The eigenfrequency $f_n$ of a piezoelectric bimorph with L>>w can be determined, such as for two types of boundary conditions: (1) anchored at one end (with maximum deflection at other end) as $$f_n = \frac{0.16T}{L^2}\sqrt{\frac{Y_{11}}{\rho}},$$

or (2) anchored at one end and with the other end immobile along the z-direction (with maximum z-deflection in the middle of the actuator length), as $$f_n = \frac{0.48T}{L^2}\sqrt{\frac{Y_{11}}{\rho}}.$$

While neither of these boundary conditions corresponds exactly to our experimental conditions, e.g., in which one entire side of the actuator 152 can be taped onto the sealing PDMS membrane overlayer 150 of the microfluidic chip 100, we found the latter to be in better agreement to our measurements.

Figure 4:
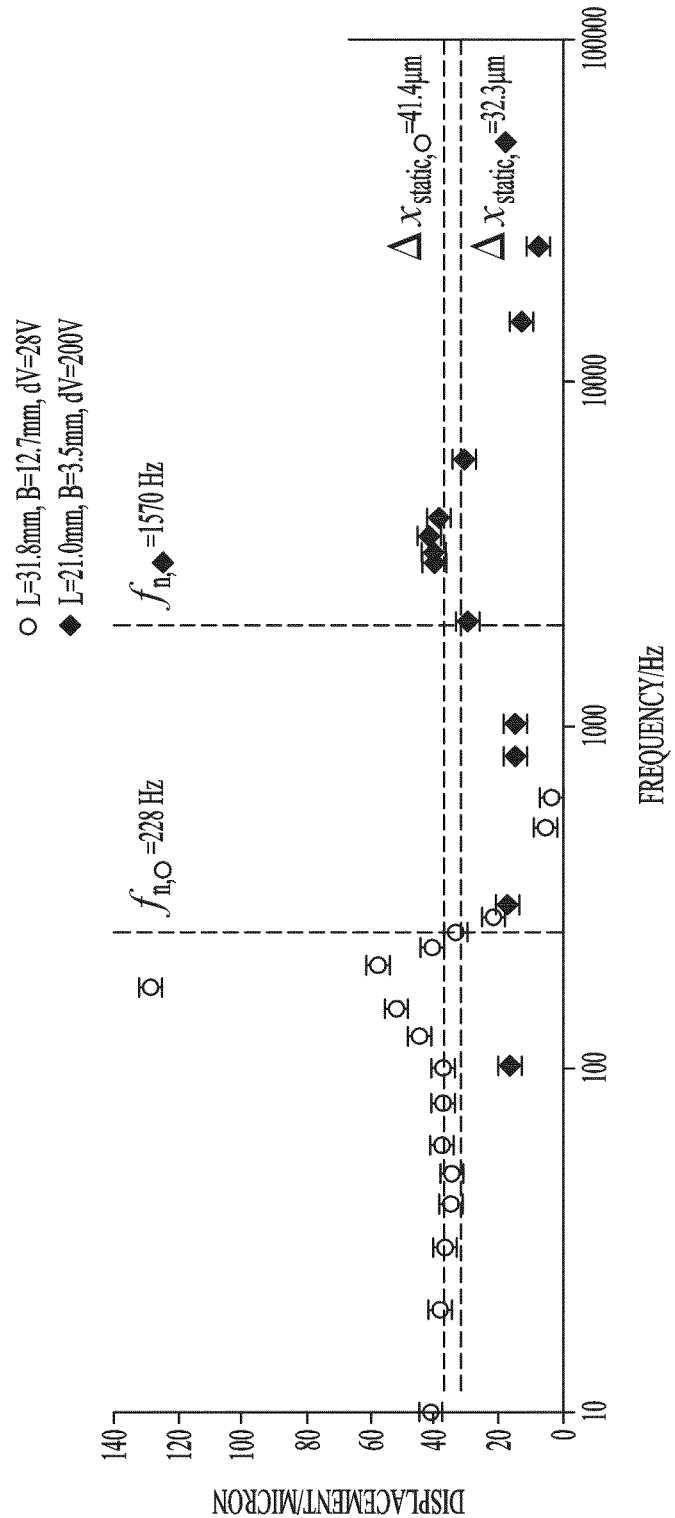
FIG. 4 is an example of a graph of displacement vs. frequency, illustrating an example of influence of the excitation frequency on the amplitude of the actuator motion.

FIG. 4 shows an example of a graph of displacement vs. frequency, illustrating an example of influence of the excitation frequency on the amplitude of the actuator motion. In the example of FIG. 4, the empty circles and full lozenges denote two types of boundary conditions as described above. The actuator size and excitation amplitude are given in the legend. The dashed lines denote the theoretical values for natural frequency and static displacement.

The experimental data represented in FIG. 4 was obtained using an Optem long distance microscope objective and a high-speed camera. This allowed us to measure an example of the temporal deformation of an actuator driven by a single rectangular pulse of amplitude dV and duration $(2f)^{-1}$. FIG. 4 summarizes an example of these measurements, showing an example of the maximum observed displacement as a function of the frequency f of the driving pulse. In the example of FIG. 4, a first series of measurements, shown by empty circles, can be made for a relatively large bimorph clamped at one end, with dimensions given such as described above. Theoretical values can also be plotted as dashed lines for both the maximum static displacement and the eigenfrequency. The agreement between theory and experiment can be relatively good in terms of resonance frequency and static (low frequency) displacement. The lower resonance frequency observed experimentally can be explained by the difficulty to experimentally perfectly anchor one end of the actuator, because we used a C-clamp, in certain examples. A second series of measurements can be made with a smaller actuator attached such as via double-sided tape to a 180 μm thin PDMS layer, e.g., mounted as in the actual microfluidic chip 100. The two ends of the PDMS layer can then be anchored firmly between two C-clamps. Each C-clamp can be about 1.5 mm away from the corresponding end of the piezoelectric actuator. While both the actuator size and configuration can be close to the design used in conjunction with the microfluidic chip 100, the configuration is close but not exactly corresponding to the second type of boundary condition presented above. This may explain why the measured static displacement and resonance frequencies are different, both being larger than the theoretical values. Also, the recorded motion shows that the actuator ends do not move, the larger deformation occurs between these ends, the actuator vibrating in its first mode. In this example, the visualization shows that the actuator does not cease its motion when the driving pulse is removed. Instead, the actuator keeps oscillating at its natural frequency for about 6 periods, at which time the amplitude of the oscillation becomes lower than the spatial measurement error. This behavior, in which the reagent chamber 108 experiences residual oscillations, can be due to the relatively large size and inertia of the actuator, and the very soft, thin PDMS sealing layer 150 upon which the actuator 152 is attached. This behavior contrasts with a piezoelectric drop-on-demand approach in which the chamber walls are much stiffer, such as made of non-compliant glass or silicon; in such cases the chamber deformation is in direct linear relationship to the applied voltage pulse. Any theoretical modeling of the in-chip drop-on-demand process presented here can take into account the residual oscillations of the actuator 152 and the frequency response curve of the actuator 152 and chamber 108 system.

Example of Effects of Driving Pulse on the Drop Formation

In-chip microfluidic drop-on-demand generation can be a complex fluid dynamics process involving moving solid boundaries, acoustic wave propagation, and a highly deforming liquid-liquid interface. Several aspects of the drop generation process can be adjusted to provide an on-demand microfluidic droplet generator, such as the precise control of the drop volume and motion, the elimination of smaller satellite drops (if desired), and the management of cross-talk effects such as in designs with multiple nozzles 112. Each of these aspects can be affected by the design geometry and the actuation process. In one approach to a drop-on-demand generator, the fluidic part is made of stiff materials. This can efficiently transport the pressure wave from the actuation site to the nozzle where the drop is generated. The present approach, however, can provide a device that can behave differently. In an example of the present approach, the soft compliant PDMS rubber walls of the reagent chamber 108 reduces the apparent speed of sound in water, and dampens the acoustic pressure wave. This can reduce cross-talk effects in a microfluidic chip 100 that includes multiple nozzles 112, but may use more energy to generate a drop.

Figure 5:
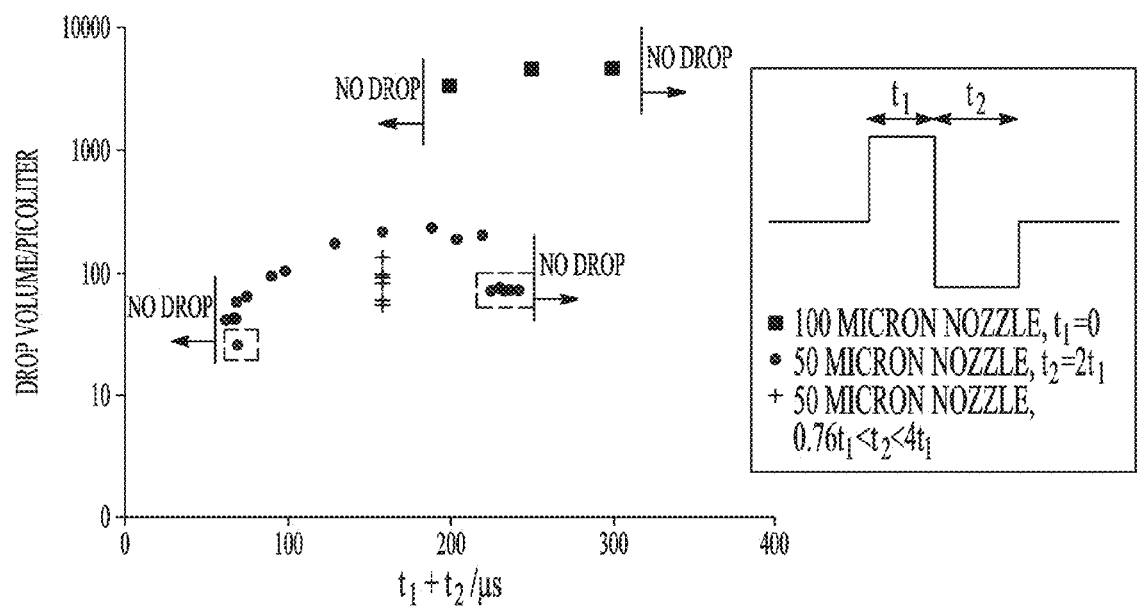
FIG. 5 is an example of a graph of drop volume (pL) vs. time (μs) illustrating how drop volume is affected by various drop dispensing parameters, such as nozzle size, pulse shape, or pulse length.

FIG. 5 is an example of a graph of drop volume (pL) vs. time (μs) illustrating how drop volume can be affected by various drop dispensing parameters, such as nozzle size, pulse shape, or pulse length. In the example of FIG. 5, the horizontal axis denotes the total pulse length, which involves the chamber expansion followed by the chamber compression, with respective duration $t_1$ and $t_2$. The nozzle width is indicated in the legend, and the channel height is the same as the nozzle width. The dotted rectangles show doublet dispenses, in which two drops of smaller volume are generated concurrently by a single pulse.

The characterization experiments reported in FIG. 5 describe how the drop volume can be influenced by the nozzle size, the pulse shape and the pulse duration. The data in the example of FIG. 5 was obtained using a piezoelectric actuation voltage of +/−200V. The length of the reagent chamber 108 used for the respective 50 and 100 μm nozzle case were 12 mm and 20 mm, respectively, in this example. Note that the volume of the reagent chamber 108 in this example is about 10 nL, which is about $10^5$ bigger than a 100 pL volume drop. Such a pre-filled reagent chamber 108 can generate a large amount of drops of interest before needing refilling. After each drop dispense, we observed that the meniscus typically returns to its initial location within a few milliseconds. In this example, the shape of the pulse corresponds to an initial expansion of the reagent chamber 108 for a time $t_1$ followed by compression of the reagent chamber 108 for a time $t_2$. Pulses with $t_1=0$ were also successful at generating a drop; such a pulse corresponds to a compression of the chamber. The y-axis of FIG. 5 shows that drops with volumes from 25 pL to 4.5 nL can be generated, such as by varying the actuation pulse shape and the size of the nozzle 114 (which corresponded to the height of the channel 102). This is a remarkable range that is larger than two orders of magnitude. For a given geometry of the nozzle 114, FIG. 5 also shows that the drop volume can be controlled by the pulse shape within one order of magnitude. For example, the 50 μm nozzle can produce drops in the 40-300 pL range. In this example, pulses with durations that are too different from an optimum duration did not produce any drop, as shown by the arrows in FIG. 5. Without being bound by theory, this may be because surface tension forces are strong enough to pull back the meniscus in the case of a short pulse or that a given pulse duration is needed to generate and amplify an unsteady pressure wave in the chamber. For the 50 μm nozzle we can also observe some dual-dispense states for pulses close to the states in which no drop is ejected. A dual-dispense state can correspond to a case in which two smaller drops are concurrently produced, such as by the doublet instability process described and shown below. In an example, drop volume can be controlled, such as by changing the ratio between the expansion time and the compression time, while keeping the total actuation time constant. We did not systematically investigate the effect of the chamber length, but we found that a long chamber (e.g., 20 mm) produces drops in an easier manner. Experiments with a middle-length chamber (e.g., 12 mm) produced drops for only the maximum actuation voltage, and tests with a shorter chamber (e.g., 6 mm) did not produce any drop, although the meniscus motion was clearly visible.

The results in FIGS. 4 and 5 mean that an optimum pulse duration to produce drops corresponds to the natural frequency $f_n$ of the actuator. Indeed, the second equation for natural frequency presented above predicts values off, of 1.57 kHz and 4.74 kHz, respectively, for the actuators 152 of the chambers 108 with the 100 μm and 50 μm nozzle 114, respectively. The corresponding single pulse duration for the 100 μm nozzle 114 would be $t_2=1/(2 f_n)=318$ μs, a time close to the 180-300 μs interval effective at producing drops in the example of FIG. 5. Similarly, the corresponding total pulse duration for the 50 μm nozzle 114, in the case of a pulse with $t_1=t_2$, would be $t_1+t_2=1/f_n=211$ μs, a time close to the 60-220 μs interval effective at producing drops in FIG. 5. The fact that the pulse duration estimated theoretically is at the higher end of the interval of experimentally successful durations may indicate that the actual value of $f_n$ is slightly higher than the theoretical value, as shown in FIG. 4 and explained above by the difference of boundary conditions between the experiments and the theory.

Figure 6:
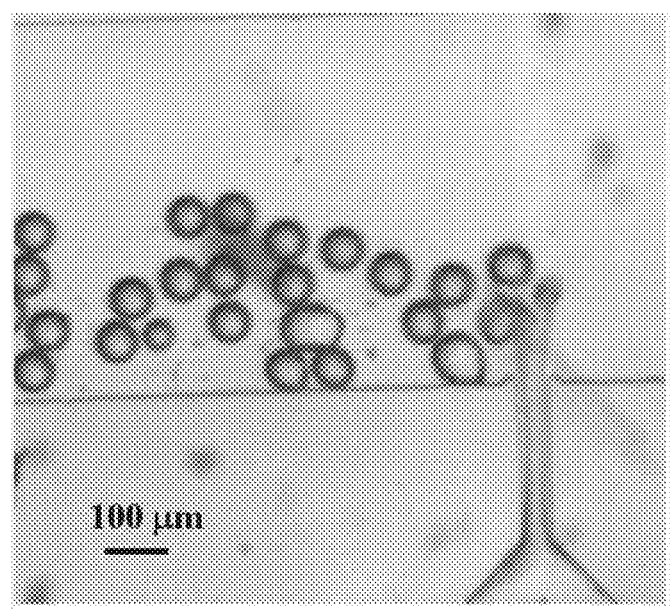
FIG. 6 shows a case in which a pulse can be applied continuously to generate a train of drops, such as at 2.5 kHz.
Figure 7A:
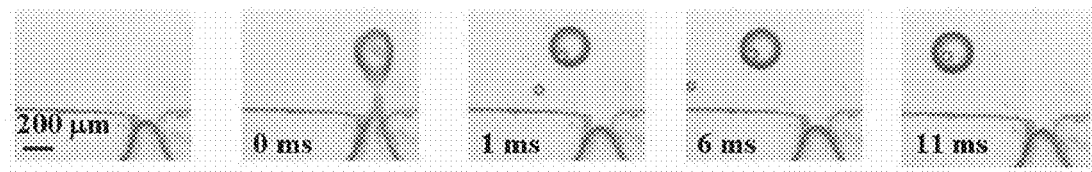
FIG. 7 presents experimental images showing examples of four features of the present in-chip drop-on-demand with relevance to lab-on-a-chip applications.
Figure 7B:
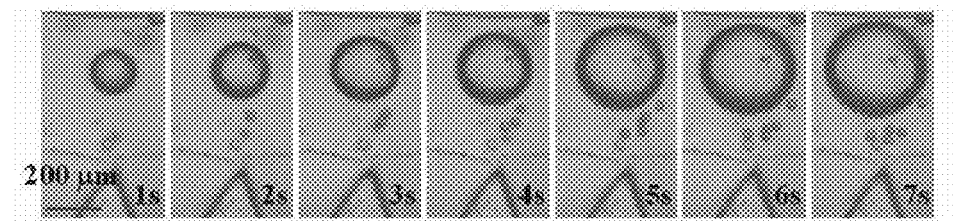
Figure 7C:
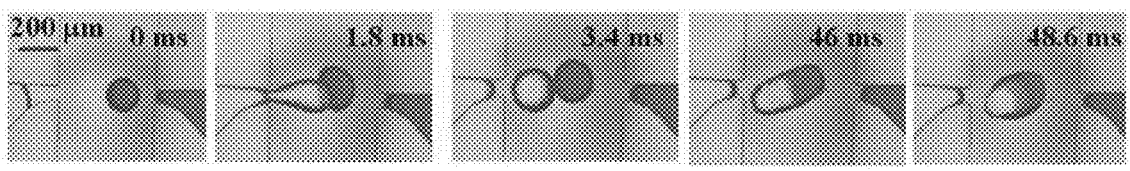
Figure 7D:
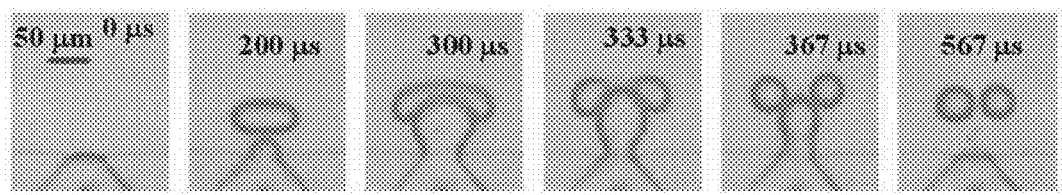
Figure 7E:
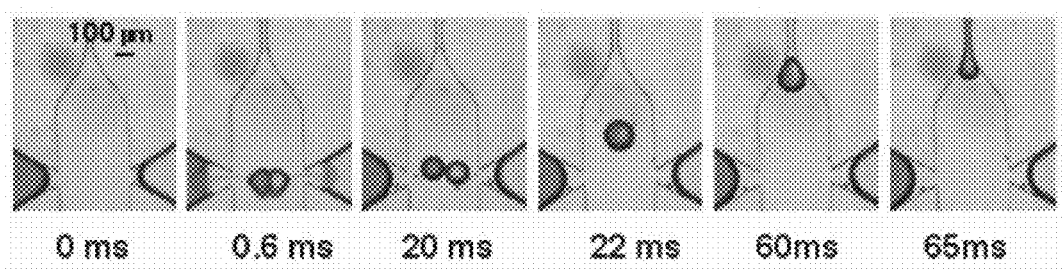

We also tried to quantify the maximum dispense rate by repeating the driving pulse using smaller time intervals between pulses. Our experiment shows that drops can still be generated even if the time interval is reduced to 0 seconds, which corresponds to applying the drop generation actuation pulse continuously. FIG. 6 shows a case in which a 400 μs pulse, shaped as in FIG. 5 with $t_2=2t_1$, can be applied continuously to generate a train of drops at 2.5 kHz. Note that, in this example, the nozzle 114 can include 70 μm mini-channel that is 200 μm long, which opens up in fluid communication with a wider (e.g., about 200 μm-250 μm) main channel 102. In addition, we also studied the uniformity of the drop volumes obtained using the same nozzle 114. In an example, at a dispense rate of 6.2 Hz, 20 drops generated had an average volume of 1023 pL and a standard deviation of 16 pL, which corresponds to less than 2%.

Examples of Features and Relevance to Lab-On-A-Chip

The systems and methods described in this document can implement, using a microfluidic chip 100, a drop-on-demand technique that can provide precise, reliable control of the drop volume and drop-generation timing. The in-chip drop-on-demand technique has the potential to perform in many applications, such as in one or more of in-chip reagent mixing, transport, or multi-step reactions.

FIG. 7 presents experimental images showing examples of four features of the present in-chip drop-on-demand with relevance to micro total analysis systems (μTAS), lab-on-a-chip applications, or other applications. The frames are extracted from associated movies. In FIG. 7, image sequence (a) shows an example of drop transport by viscous drag. Image sequence (b) in FIG. 7 shows an example of "digital" control of drop volume. Image sequence (c) in FIG. 7 shows an example of merging and mixing of two different reagents, such as by using opposing nozzles 114. Image sequence (d) in FIG. 7 shows an example of a doublet dispense, in which two drops of small volume are concurrently generated by a single actuation pulse. Image sequence (e) in FIG. 7 shows another example of merging and mixing of two different reagents, such as by using opposing nozzles 114.

Image sequence (a) of FIG. 7 shows an example of an ability to transport the dispensed drop away from the dispensing nozzle 114, along the main channel 102. This feature can be realized by dispensing the drop into the main channel 102, in which the fluid is moved by a syringe pump at one or more of the inlet 104 or the outlet 106 of the channel 102. In this experimental example, the measured drop velocity along the channel 102 is 7 cm/s. This motion of one or more dispensed drops by viscous drag can also be used in a flow focusing device. It can be useful to the in-chip drop-on-demand technique, because transporting a droplet from the shooting area of one nozzle 114 to that of another can allow multi-step reactions to be carried out, such as at frequencies of several Hertz. Interestingly, the image sequence (a) of FIG. 7 shows a smaller particle embedded in the main drop. This phenomenon can be suppressed or encouraged, such as by adjusting the actuation pulse shape and intensity. The ability to dispense a drop that encapsulates another liquid, a solid, or a gas can be of interest, such as for manufacturing complex multiwall or hollow spheres. In certain examples, this can be used to encourage a single drop, bubble, or other particle to encapsulate or include a biological cell or other similarly sized object, such as a 10 micrometer bead, for example. Similar considerations can be made for the smaller satellite drop generated between the drop and the nozzle, such as shown in the image sequence (a) of FIG. 7. Issues related to satellite drop formation can merit attention in certain applications (e.g., in printing application because such satellite drops may have relevance to printing quality).

Image sequence (b) in FIG. 7 shows an example of a second feature, which can include the ability to "digitally" control the dispensed drop volume, such as by generating one or more additional drops that coalesce with the original drop to increase its drop volume. The first frame of image sequence (b) in FIG. 7 shows an example of a 500 pL initial drop, the volume of which can be increased to 3.5 nL, such as by generating six successive incremental 500 pL drops that successively coalesce with the initial drop. This coarse, "digital" way to control the drop volume by issuing multiple drops that coalesce into a combined drop can be used with or without the finer, "analog" volume control that can be obtained, such as by modifying the pulse parameters, such as described above, to more exactly dispense the desired quantities over a wide range of volumes. While in-flight coalescence can be obtainable by an "atmospheric" approach, in which drops can be jetted into the air, the present in-chip drop-on-demand approach can more easily obtain drop coalescence, because the dispensed drop becomes immobile in the main channel 102 after the kinetic energy of the dispensing has been dissipated. The walls of the channel 102 shown in the image sequences (a) and (b) of FIG. 7 can be irregular. The nozzles 114 used in these experiments were manufactured during preliminary experiments in which the master was a piece of electric tape applied to a glass slide, and approximately cut to the desired geometry with a sharp cutter under a stereo microscope. Large drops, such as were created as shown in the image sequence (b) of FIG. 7 can be split into smaller drops, if desired, such as by moving them into a T-shaped or like connection.

Image sequence (c) of FIG. 7 shows an example of how different reagents can be mixed into a single drop. This example can make use of two opposing nozzles 114, such as facing each other on opposite sides of the same channel 102, from respective reagent chambers 108 that are also located across the channel 102 from each other. In the example shown in the image sequence (c) of FIG. 7, first, the nozzle 114 on the right can generate a first drop (e.g., ink). Then, the left nozzle 114 can generate a first drop (e.g., pure water), which hits the first drop. In this example, coalescence of the first and second drops then occurs at t=46 ms. This starts the mixing of the substances of the first and second drops (e.g., ink and water), such as through diffusion and the transient flow associated with the coalescence. In the example of image sequence (c) of FIG. 7, coalescence does not occur immediately after the first and second drops hit each other.

Image sequence (e) of FIG. 7 shows another example of how different reagents can be mixed into a single drop. As in image sequence (c), image sequence (e) was made using a system that includes two opposing nozzles 114 facing opposite one another across channel 102. The left nozzle disperses a drop of ink, while the right nozzle dispenses a drop of water. Coalescense occurs at approximately t=22 ms. before the drop is transported by viscous drag into a contraction where mixing will be enhanced.

Without being bound by theory, this is probably because of the thinning and breakup of an oil film between the first and second drops, such as is the case when the channel 102 is filled with oil into which the first and second drops are dispensed. This delay can be reduced, such as by oppositely charging the first and second drops. Mixing and particle transport of the drop can be controlled such as by vibrating the liquid with the same piezoelectric actuators that generate the drops. To some extent, the mixing process presented here can be compared to an "airborne chemistry" approach, in which a drop can be immobilized in the air at a node of a high-power ultrasound field. In an airborne chemistry approach, this main drop can then act as an isolated reactor fed by smaller drops of reagent dispensed by atmospheric nozzles. Airborne chemistry can be used for screening the conditions for protein crystallization or for performing biological analyses. In certain examples, the present in-chip drop-on-demand can allow the drop dispensed in an immiscible fluid to function as an isolated reactor, such as can be fed by further additions of the same or other reagents from the same or neighboring nozzles. Optical measurements might be more difficult in some embodiments of the present inventive technique, such as those that utilize a flow of hexadecane in channel 102 and/or those that use a PDMS wall to form a portion of channel 102. However, in those embodiments, the surrounding hexadecane can allow higher heat transfer and can suppress evaporation.

Image sequence (d) of FIG. 7 shows an example of another feature: the ability to generate a doublet of drops, if desired, in response to applying a single excitation pulse to the actuator. In certain examples, this can occur when an initially generated drop is hit by a strong subsequent excursion of the meniscus. During this process, the meniscus can break the initial drop into two half-drops, while briefly assuming the shape of a cartoon character (see, e.g., image sequence (d) at 367 µs). We call this type of drop dispensing the doublet dispense. To the best of our knowledge, no doublet dispense has ever been realized with an atmospheric drop-on-demand technique because, in an atmospheric technique, the dispensed drop would quickly travel away from the nozzle area where the meniscus oscillates.

Figure 8:
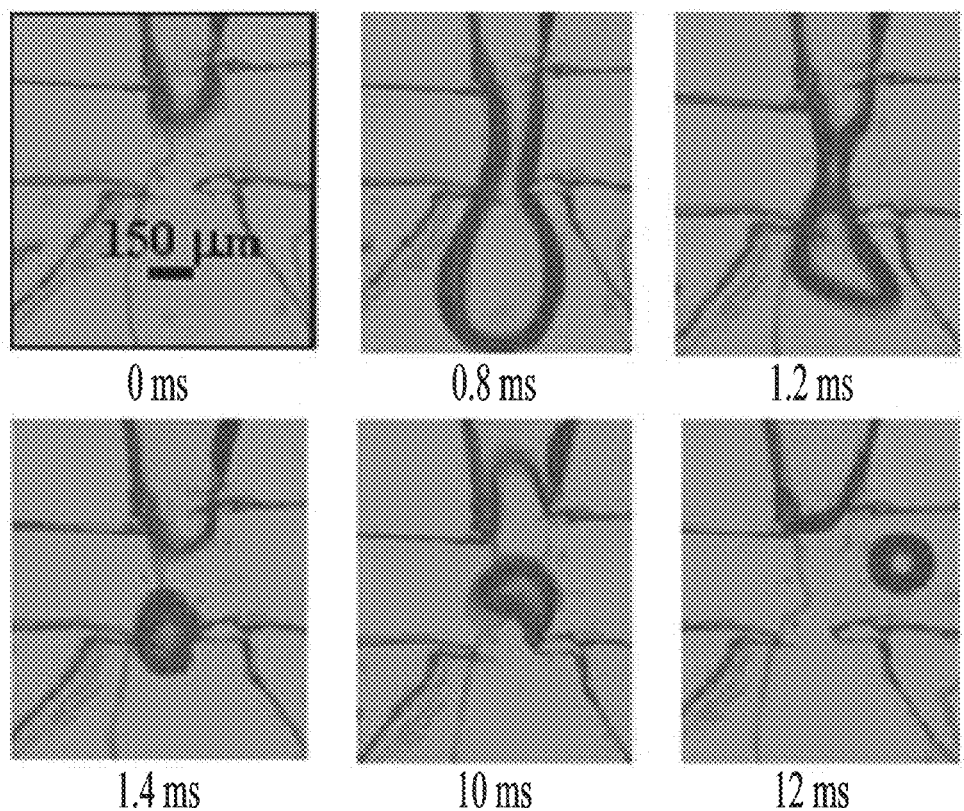
FIG. 8 shows an example of how a similar piezoelectric technique can be used to generate a single gas bubble on-demand using a microfluidic chip.

FIG. 8 shows an example of how a similar piezoelectric technique can be used to generate a single gas bubble on-demand using a microfluidic chip. In this example, two reagent chambers 108 can be located on opposite sides of a microfluidic channel 102. A first one of the reagent chambers 108 can carry a liquid or other fluid (e.g., gel or other flowable non-gaseous substance) for the bubble, while a second one of the reagent chambers can carry the gas for the bubble. Expansion of the liquid/fluid first reagent chamber 108 can be used to draw gas into the liquid/fluid reagent chamber 108 from the opposing gas second reagent chamber 108. Then, the liquid/fluid first reagent chamber can be compressed to expel the gas bubble into the microfluidic channel 102.

In another approach, the liquid/fluid first reagent chamber 108 could be first compressed, such as to push liquid or fluid into the gas second reagent chamber 108, and then the liquid/ fluid first reagent chamber 108 can be expanded, such as to draw the liquid/fluid and gas out of the gas second reagent chamber 108. This can be used to expel a bubble into the microfluidic channel 102, or to draw gas into the liquid/fluid first reagent chamber 108, which can then be compressed to expel a gas bubble into the microchannel 102.

Figure 10:
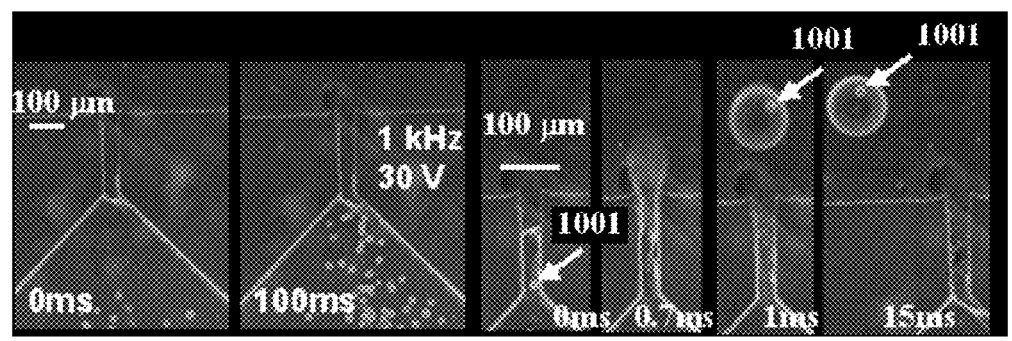

FIG. 10 shows an example of how a similar piezoelectric technique can be used to form an encapsulated particle on-demand using a microfluidic chip. In this example, a reagent chamber 108 is filled with a mixture or water and small beads. The beads are approximately the same size as a single biological cell. First, a low amplitude vibration from an actuator draws one of the beads 1001 towards the meniscus. Then a second, stronger, pulse from the actuator generates a single drop encapsulating bead 1001. This method could be used to encapsulate other types of particles, such as one or more biological cells. This method can also use other types of liquids in the reagent chamber (e.g., a fluid that is biologically compatible with a cell of interest).

Furthermore, the present methods can also be used to encapsulate small particles. For example, the methods of mixing reagents in a single drop (e.g., those described above in relation to FIG. 7(e)) can be used to mix a reagent with an encapsulated particle and/or two or more species of particles in a single drop. In an example, the first reagent chamber can be filled with a fluid of interest (e.g., a reagent or mixture of reagents) or one or more species of a first particle (e.g., a first species of biological cells) while the second reagent chamber can be filled with the same or different fluids or particles (e.g., a different reagent or species of particle(s)). When drops are dispensed from each reagent chamber and coalesce, the final merged drop could contain a combined mixture of reagents and particles from the two reagent chambers. These encapsulation examples are particularly well suited for performing single-cell analysis in biological studies.

Figure 9:
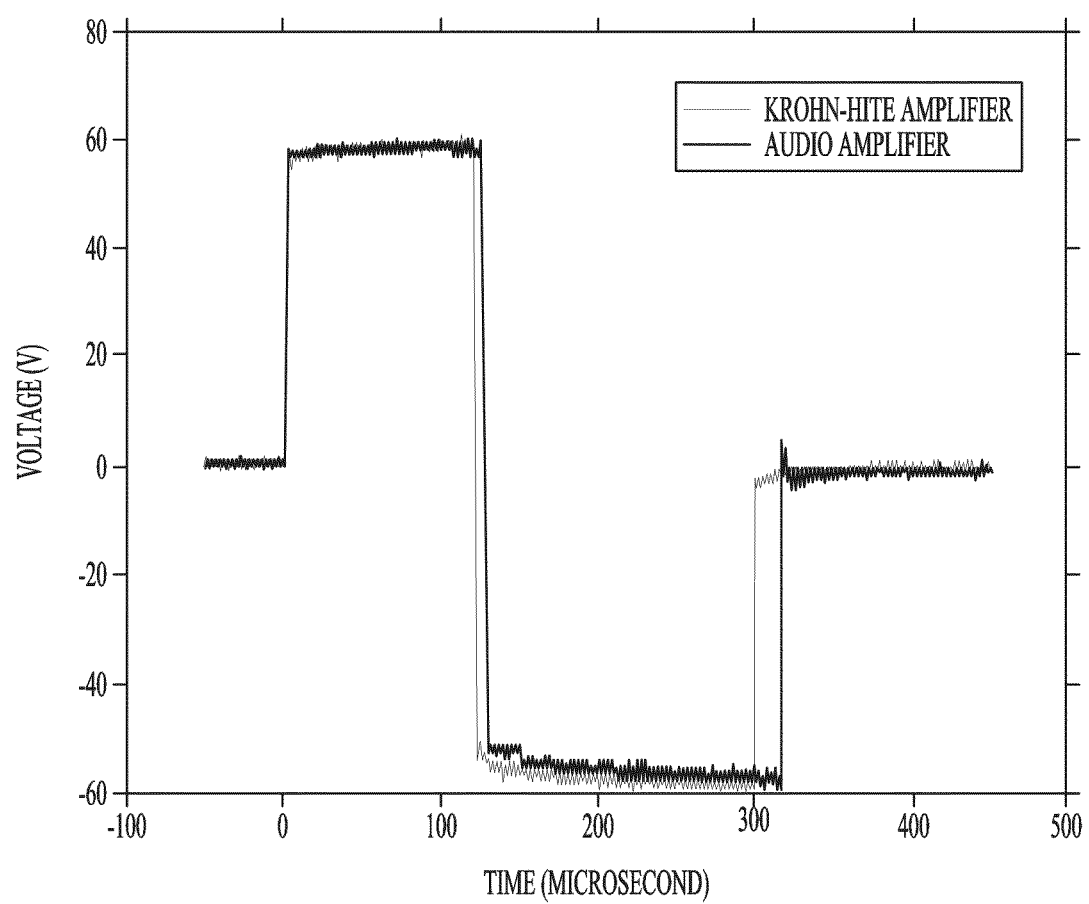
FIG. 9 compares pulses between research and audio amplifiers.

An interesting feature of the present in-chip drop-on-demand technique is that the piezoelectric excitation frequencies used to produce drops can be on the order of a few kHz, such as described above. This is within the audio frequency range. Therefore, a research-grade pulse generator and amplifier used to drive the actuators can be replaced by inexpensive audio components. For example, audio amplifiers can be mass-produced and can offer multi-channel capabilities, for example, such as up to eight channels for a $300 home cinema amplifier. We tested this hypothesis by powering a microfluidic chip with a used audio home stereo amplifier ("g" in FIG. 2) (JVC AX-R87, 4 channels, 400 W, $37 on a popular auction site). With the same piezoelectric actuator as a load, the pulses amplified by the research-grade Krohn-Hite amplifier and the audio amplifier are compared in FIG. 9, which shows a good amplifying quality of the audio amplifier, with some minimal noise and a pulse about 6% longer. We also tried to connect the input of the home amplifier to the sound card of a laptop computer ("f" in FIG. 2), and found that the meniscus moves quite well to the melodies and rhythms of the song "New York USA" from French artist Serge Gainsbourg. The signal of this song and a few others were not adequate to produce single drops, however we managed to produce a single drop on demand by driving the actuator with the home audio amplifier connected to a function generator. This ability to drive an actuator 152 of a microfluidic chip 100 with inexpensive, mass-produced audio electronics can be valuable. We believe that the microfluidics growth can benefit from low-cost actuation schemes instead of the expensive components of other approaches.

Discussion of Some In-Chip Drop-On-Demand Examples

The in-chip drop-on-demand techniques such as described above can, in certain examples, allow the individual on-demand generation of one or more drops of one or more aqueous reagents in a microfluidic chip, with a temporal precision of about one millisecond, and at drop generation rates exceeding 1 kHz (e.g., droplet generation time on the order of 1 millisecond). In certain examples, the ability to precisely trigger the drop generation time can allow generating one or more drops to be coordinated with one or more other events occurring in the microfluidic chip 100 or elsewhere. Examples of such events can include, by way of example, but not by way of limitation, the detection of a chemical reaction or a temperature change, the transit of one or more biological cells or other particles, or any other desired triggering event. In certain examples, the drop volume can be controlled from about 40 pL to about 4.5 nL, such as by varying the actuation pulse shape, the geometry of one or more portions of the microfluidic chip 100, or by merging several drops together, such as described above. Because the generated drop is surrounded by an immiscible fluid, evaporation can be inhibited or prevented, heat transfer can be enhanced, and the fluid can be used to transport the drop by viscous drag. As discussed above, the dead volume can be quite small. A typical reagent chamber 108 filled with a few microliters can dispense several thousands drops with a typical volume of 100 picoliters.

The present in-chip microfluidic drop-on-demand techniques can be compared to certain digital microfluidic approaches. The present techniques can work with any aqueous fluid, not just dielectric fluids, and can dispense smaller drops, if desired. In terms of mixing speed and ability to encapsulate one or more reagents within an immiscible liquid, the present in-chip drop-on-demand techniques can, in certain examples, be comparable to a segmented flow approach, but offering more flexibility because in the present in-chip drop-on-demand approach, each single droplet generation event can be individually triggered and controlled. Also, as described above, actuation in the present system can be driven using inexpensive, mass-produced audio electronics, which can help commercial adoption of this technology.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
a microfluidic chip including
    a microchannel that includes a microchannel inlet and a microchannel outlet and a first reagent chamber that includes a first chamber inlet, a first reagent chamber outlet configured to provide fluid communication between the first reagent chamber and the microchannel, and a first compliant wall, wherein the first chamber inlet is separated from the first chamber outlet and the microchannel by a portion of the first reagent chamber that includes the first compliant wall;
a first actuator coupled to the first compliant wall of the first reagent chamber and configured to actuate a volume change of the first reagent chamber in response to a first control signal; and
a controller configured to apply the first control signal to the first actuator to perform the actuating of the first compliant wall of the first reagent chamber to controllably and individually dispense a first fluid particle on-demand from the first reagent chamber into an immiscible fluid in the microchannel.

2. The apparatus of claim 1, wherein the controller is configured to provide an actuation control signal having a timing accuracy on the order of nanoseconds.

3. The apparatus of claim 1, wherein the controller is configured to apply the first control signal to dispense particles on-demand at a repetition rate in excess of a value that is on the order of kiloHertz.

4. The apparatus of claim 1, wherein the first fluid particle has a volume that is between about 25 pL and about 4.5 nL.

5. The apparatus of claim 1, wherein the first chamber outlet includes a first nozzle having a first nozzle width that is in a range between about 25 μm and about 100 μm.

6. The apparatus of claim 1, wherein the first compliant wall includes a PDMS membrane and the first reagent chamber further includes compliant PDMS sidewalls supported on a rigid substrate.

7. The apparatus of claim 1, comprising:
a second reagent chamber that includes a second chamber inlet, a second chamber outlet located within a particle dispensing range of the first chamber outlet and configured to provide fluid communication between the second chamber and the microchannel, and a second compliant wall;
a second actuator coupled to the second compliant wall of the second reagent chamber and configured to actuate a volume change of the second reagent chamber in response to a second control signal; and
wherein the controller is configured to apply the second control signal to the second actuator, independently from the first control signal applied to the first actuator, to perform the actuating to controllably and individually dispense a second fluid particle on-demand from the second reagent chamber into the immiscible fluid in the microchannel.

8. The apparatus of claim 7, wherein the first reagent chamber is configured to carry a gaseous substance, the second reagent chamber is configured to carry a liquid or other substantially non-gaseous fluid substance, and wherein the controller is configured to operate at least one of the first and second actuators to expel a gas bubble into the microchannel.

9. The apparatus of claim 8, wherein the controller is configured to operate the second actuator for expanding the second reagent chamber to draw gas from the first reagent chamber, and wherein the controller is configured to expel the gas bubble by providing the second control signal for actuating a compressing of the second reagent chamber.

10. The apparatus of claim 7, wherein the first and second chamber outlets are located across and opposite the microchannel from each other.

11. The apparatus of claim 7, wherein the first compliant wall is an overlying membrane that is affixed to a top surface of the microfluidic chip and configured to seal the microfluidic chip.

12. The apparatus of claim 11, wherein a portion of the overlying membrane is positioned over the microchannel.

13. The apparatus of claim 1, wherein the first reagent outlet tapers to the first reagent outlet.

14. An apparatus comprising:
a microfluidic chip including
    a microchannel that includes a microchannel inlet a microchannel outlet, and an immiscible fluid;
    a first reagent chamber that includes a first fluid, a first chamber inlet, a first chamber outlet providing fluid communication between the first reagent chamber and the microchannel, a first fluid; and a compliant membrane affixed to a top surface of the microfluidic chip forming a first compliant wall of the first reagent chamber;

a first actuator coupled to the first compliant wall of the first reagent chamber and configured to actuate a volume change of the first reagent chamber in response to a first control signal; and a controller configured to apply the first control signal to the first actuator to perform the actuating to controllably and individually dispense a first fluid particle on-demand from the first reagent chamber into the immiscible fluid in the microchannel.

* * * * *